United States Patent [19]  [11] 3,951,945
Heesen et al. [45] Apr. 20, 1976

[54] METHOD FOR THE PREPARATION OF ESTERS OF POLYALCOHOLS

[75] Inventors: Jan Gerhard Heesen, Gorinchem; Pieter Koenraad Kuipers, Woudrichem; John Adriaan van Velthuijsen, Gorinchem, all of Netherlands

[73] Assignee: B.V. Chemie Combinatie Amsterdam C.C.A., Amsterdam, Netherlands

[22] Filed: May 10, 1974

[21] Appl. No.: 468,738

[52] U.S. Cl. .................. 260/210 R; 260/234 R; 260/410.6; 260/410.7
[51] Int. Cl.² .......................................... C08B 37/00
[58] Field of Search ......... 260/234 R, 410.6, 210 R, 260/410.7

[56] References Cited
UNITED STATES PATENTS

| 3,347,848 | 10/1967 | Ismail et al. | 260/234 R |
| 3,631,025 | 12/1971 | Martin | 260/234 R |
| 3,792,041 | 2/1974 | Yamagishi et al. | 260/234 R |

*Primary Examiner*—Lewis Gotts
*Assistant Examiner*—Cary Owens
*Attorney, Agent, or Firm*—Haseltine, Lake & Waters

[57] ABSTRACT

A process for the preparation of carboxylic acid esters of linear aliphatic polyalcohols or of hydrophilic derivatives of these polyalcohols containing a minimal percentage of anhydrocompounds, the process comprising esterifying an aliphatic fatty acid having 10 to 22 carbon atoms with a polyalcohol or a glycoside thereof in the presence of a fatty acid soap, at a temperature between 100° and 190°C while simultaneously eliminating water formed during the reaction. The polyalcohol is a linear aliphatic polyalcohol of the formula $C_nH_{n+2}(OH)_n$ wherein $n$ is at least 4. Optionally the obtained esters can be further converted. Products are obtained which are useful, for example, as emulsifying agents and baking additives.

18 Claims, No Drawings

METHOD FOR THE PREPARATION OF ESTERS OF POLYALCOHOLS

Esters of polyalcohols and higher fatty acids are frequently used non-ionic emulsifying agents. They are prepared by esterification of, e.g. sorbitol with fatty acids at a temperature of at least 190°–200°C. During the reaction a very considerable amount of the sorbitol (i.e. more than 75%) is converted into anhydrocompounds (intramolecular ethers; monoanhydrosorbitol: sorbitan and dianhydrosorbitol: isosorbide). Due to the forming of these anhydrocompounds the products become less hydrophilic (hydroxyl groups are eliminated) and their application in foodstuffs encounters difficulties as the ethers in the body are not metabolised in the way that is normal with polyalcohols.

The preparation of polyalcohol esters of fatty acids without forming of anhydrocompounds is known by re-esterification; e.g. mannitol and sorbitol esters of fatty acids, prepared by re-esterification of, among other things, the methyl or glycerol esters in a - relatively expensive - solvent, such as pyridine, dimethyl formamide, dimethyl acetamide, dimethyl sulfoxide, N-methyl 2-pyrrolidon (U.S. Pat. No. 2,997,492, 2,997,493, 3,138,463, 3,141,012 and 3,600,186). The residues and decomposition products of such, often poisonous, solvents are difficult to eliminate from the products and this, in its turn, creates difficulties in case the products are used in foodstuffs.

Moreover, the forming of anhydroproducts of the polyalcohol can be largely prevented if, for esterification polyalcohols containing protective groups, e.g. the di-isopropylidene derivatives of sorbitol, arabitol and erythritol (U.S. Pat. No. 3,579,547), are used.

Now it was found that, with an excellent result, carboxylic acid esters of linear polyalcohols with the formula $C_nH_{n+2}(OH)_n$ (in which n is a whole number with a value of 4 or more) or carboxylic acid esters of hydrophilic derivatives of these polyalcohols can be obtained, containing a minimal percentage of anhydrocompounds, if the fatty acid is esterified with the polyalcohol or a glycoside thereof in the presence of a fatty acid soap (in a quantity of 10% or more, calculated upon the polyalcohol) at a temperature between 100° and 190°C with simultaneous elimination of the water formed during the reaction and, if desired, further conversion of the esters obtained. The esters thus obtained contain only a slight quantity of polyalcohol converted into anhydrocompounds. If, for instance, sorbitol is esterified at 150°C in the presence of a fatty anhydrocompounds (sorbitan).

It is a well-known procedure to use soap as a catalyst or as a miscibility promoting agent in preparing saccharose esters of fatty acids without a solvent (*J. Am. Oil Chemists' Soc.* 47, 56–60 (1970); Netherlands patent application Ser. No. 7,006,775) and at the preparation thereof by means of the microemulsion method (German patent application Ser. No. 1,916,886; Netherlands patent application Ser. No. 7,015,560).

In the method for the preparation of fatty acid esters of polyalcohols a good result can generally be obtained with less soap than is required in the micro-emulsion process and no homogeneous solution or micro-emulsion is present during the esterification of the greater part of the fatty acid. A characteristic difference from the well-known methods is that the method according to the invention uses fatty acids instead of methyl esters or other fatty acid esters.

The method is also very satisfactory for the preparation of fatty acid esters of glycosides of polyalcohols, particularly of lactitol and maltitol. The glycosides can be prepared by hydrogenation of reducing di- and oligo-saccharides, e.g. lactose and maltose (lactitol=4-β-D-galactopyranosyl-D-sorbitol; maltitol = 4-α-D-glucopyranosyl-D-sorbitol). The properties and applicability of the fatty acid esters of the glycosides are comparable to those of the known saccharose esters of fatty acids. The polyalcohol glycoside esters to be prepared in the manner found (with a known structure of the glycosides) are new.

By means of the novel method emulsifying agents can be prepared, the values of which for the hydrophilic-lipophilic balance vary between very wide limits as a result of modification of the percentage of mono fatty acid esters, of the choice of the fatty acid and, particularly, of the choice of the polyalcohol and/or polyalcohol glycoside.

It is also possible to modify the properties, e.g. the hydrophilic-lipophilic balance and the crystallisation behaviour (and melting points) of the obtained polyalcohol fatty acid esters by reaction of the polyalcohol esters with one or more organic acids, mostly well watersoluble, having 2 to 6 carbon atoms, or with anhydrides or esters thereof. Suitable organic acids are, among other things, acetic acid, propionic acid, lactic acid, glycolic acid, glyceric acid, succinic acid, fumaric acid or maleic acid, malic acid, tartaric acid, citric acid. As organic acids, which are watersoluble, hydroxy acids or their anhydrides, which are entirely or partly esterified with acetic acid and/or propionic acid, can also be used.

The organic acids can also be entirely or partially esterified with aliphatic alcohols having 1–18 C-atoms, e.g. ethyl lactate, mono- to tri-ethyl citrate, lauryl, cetyl or stearyl citrate; a reesterification reaction can be applied in which the (volatile) alcohols are eliminated from the reaction mixture; polyalcohol fatty acid esters can also be converted with esters of aliphatic alcohols and di- and tricarboxylic acids into mixed esters, in which the alcohol remains entirely or partially behind in the products as an ester.

In the esterification of polyalcohol fatty acid esters with acids containing more carboxyl groups, the carboxyl groups which have not reacted with the polyalcohol fatty acid ester can also be entirely or partially neutralized with appropriate alkaline reacting substances to, for instance, the sodium-, potassium and/or ammonium salts.

In the various reactions the known alkaline and acid catalysts can be used.

By these reactions compounds are obtained that are extremely suitable as e.g. emulsifying agents and as baking additives.

It is surprising that the stability of e.g. the sorbitol fatty acid esters is so high that, in the reaction with free organic acids or with anhydrides thereof, a relatively very small amount of sorbitol anhydrocompounds is formed.

In the reaction of sorbitol with lactic acid at 100°C about 15% of the sorbitol is converted into sorbitan and isosorbide after 10 hours, whereas after a 10 hours' reaction of sorbitol palmitate with lactic acid at 100°C the part of the sorbitol converted into anhydrocompounds has been increased by 4% only, that is, from about 4% to 8%; the increased stability is also clearly apparent, if an acid catalyst like p-toluene sulfonic acid, a suitable esterifying and dehydrating catalyst, is used example XXXI; comparative (examples c and d) in the preparation of lactic acid esters of sorbitol palmitate; starting with sorbitol palmitate a percentage of only 9.5 of anhydrocompounds was formed, whereas in using sorbitol and sorbitol lactate as starting materials more than 95% of the sorbitol was converted into anhydrocompounds.

The fatty acid esters of polyalcohol glycosides can of course be modified analogously.

As polyalcohols may e.g. be used threitol, erythritol, arabitol, xylitol, ribitol, sorbitol, mannitol, dulcitol, talitol, allitol, glucoheptitol, perseitol.

The polyalcohol glycosides to be esterified contain mainly glucose or galactose units as a sugar component; they are obtainable by hydrogenation of reducing di- and oligosaccharides, e.g. maltose, lactose, isomerised maltose and lactose (maltulose and lactulose), cellobiose, isomaltose, melibiose, turanose, gentiobiose. Suitable and easily available glycosides are e.g. hydrogenated maltose, hydrogenated lactose and hydrogenated technical maltose syrups.

It is clear that as starting material for the esterification mixtures of polyalcohols and glycosides may also be used.

As a fatty acid, aliphatic fatty acids, having 10–22 C-atoms or mixtures of such fatty acids are preferably used; particularly also mixed acids originating from natural fats.

In the reaction of the polyalcohols and glycosides with the fatty acids the molar ratio polyalcohol/fatty acid may amount between 4:1 and 1:5. The fact is that in the reaction, besides mono-fatty acid esters, also di-fatty acid and higher esters are formed. The quantity of, for example, mono-fatty acid esters in the product can be varied by regulating the mol proportion polyalcohol/fatty acid.

If required, the polyalcohols and polyalcohol glycosides may be brought into the reaction mixture as an aqueous solution. However, water is not an essential component of the mixture in the reaction or in a part of the reaction as in the micro-emulsion process for the preparation of saccharose esters of fatty acids.

The fatty acid soap may be added as an alkali metal salt of fatty acids or mixtures of fatty acids having 10–22 carbon atoms, or may be prepared "in situ" by adding alkali metal compounds to the reaction mixture, e.g. alkali metal hydroxides, -bicarbonates, -carbonates or alkali metal salts of volatile organic acids.

Of course mixtures of soaps of various alkali metals may be applied. The fatty acid composition of the fatty acid soap will in many cases be chosen similar to that of the fatty acid to be esterified, but this is not necessary.

The quantity of soap can vary within examples limits. As a rule it is between 10 and 80 percent by weight of the quantity of polyalcohol or polyalcohol glycoside.

By the choice of the reaction temperature and the quantity of soap the reaction velocity can be highly influenced without the formation of a too large quantity of anhydrocompounds. As in most cases the fatty acid soap should be eliminated from the reaction product after the reaction, the quantity will generally be chosen as low as possible.

The reactions are usually carried out in the presence of an inert gas, under exclusion of oxygen.

The reaction products can be purified by known methods. It is found that the methods described for saccharose esters of fatty acids (e.g. Dutch patent application Ser. No. 70,01639) can be successfully applied for the purification of the polyalcohol glycoside esters, but also for the polyalcohol fatty acid esters.

Usually, the products are purified by extraction of the watersoluble components, e.g. non-esterified polyalcohol or polyalcohol glycoside.

The reaction product is dissolved in a suitable solvent, e.g. butanone, methyl-isobutylketone, n-butanol, ethyl acetate. After acidification of the fatty acid soap with e.g. phosphoric acid, extraction with water is applied at an increased temperature of about 50°–90°C.

Non-esterified fatty acid, mainly from the fatty acid soap, can be removed, e.g. by reaction with bivalent cations, such as calcium compounds, with formation of insoluble calcium fatty acids salts and subsequent filtration, by treatment with ion exchange resins, by fractionated crystallisation or a similar treatment, by (molecular) distillation.

According to the colour obtained the products may be subjected to a decolourising treatment with, e.g. activated charcoal, fuller's earth or hydrogen peroxide.

The solvent is usually removed by distillation under reduced pressure.

The acid value and the saponification value (expressed in mg KOH per gram product) are determined in the usual manner.

Melting points are measured by means of a melting point microscope.

The quantity of anhydrocompounds of the polyalcohols formed and the polyalcohol percentages are determined by gas-chromatography. For that purpose the products are saponified, the salts obtained are removed by means of ion exchange resins and, after adding of an internal standard if necessary, the polyalcohols are acetylated. (500 mg polyalcohol with 5.0 ml acetic anhydride in 2.5 ml pyridine, for 1 hour at 110°C). The mixture of the acetylation is analysed by means of a gas chromatograph with flame ionisation detector (column: 9 feet × ⅛ inch; stationary phase 5% XE-60 on chromosorb W-AW-DMCS; temperature 200°C). In this manner are separated e.g. sorbitol, mannitol, sorbitan (5 peaks) and isosorbide; for the analysis or sorbitol-esters mannitol is an appropriate internal standard.

The fatty acid compositions and percentages are determined by means of gas-chromatographic analyses of the methyl esters, which are generally prepared by methylation with a solution of diazomethane in diethyl ether; margaric acid was an appropriate internal standard. Gas-chromatographic columns (10 feet × ⅛ inch) are used with as stationary phases 10% DEGS and 3% OV 17 on chromosorb W-AW-DMCS; the temperature is programmed from about 100°C to 200°C and 300°C respectively.

Apart from the determination by means of gas-chromatography of the trimethylsilyl derivatives, polyalcohol glycosides can also be determined by means of quantitative thin layer chromatography. The components are separated on silica gel thin layer plates by elution with a mixture of chloroform, acetic acid and methanol (37.5, 43.0 and 6.3 parts by volume respectively) in a "flow through" development chamber according to Brenner and Niederwieser, for 8 hours. The components separated are coloured by spraying with an anilinediphenylamine-phosphoric acid reagent (dissolve 0.75 g aniline, 0.75 g diphenylamine in 50 ml ethanol and add 5 ml 85 percent phosphoric acid) and a reaction for 30 minutes at 110°C. The concentrations are measured on the plate by means of a Vitatron TLD 100 "flying spot" densitometer, in respect of standard mixtures of known concentrations.

The composition of the polyalcohol fatty acid esters and the polyalcohol glycoside fatty acid esters is determined by means of quantitative thin layer chromatography. Mono-fatty acid esters, di-fatty acid esters and higher esterified components are separated on silica gel thin layer plates by elution with a mixture of benzene, ether and methanol (70, 35 and 7 parts by volume respectively) for the determination of polyalcohol fatty acid esters, by an elution with a mixture of chloroform, acetic acid, methanol and water (80, 10, 8 and 2 parts by volume respectively) for the determination of the glycoside esters.

The retention times of the various components of which the maltitol and lactitol fatty acid esters consist, fairly well correspond with those of saccharose fatty acid esters. The esters separated are made visible by charring at 190°C, after spraying with 10% sulphuric acid. The concentrations are measured on the plate by means of a Vitatron TLD 100 "flying spot" densitometer, in respect of standard mixtures with known concentrations.

According to the process of the invention a considerable quantity of products with highly different properties can be prepared, which can be used in numerous applications, in analogy with and often with an advantage over the usual (ester) emulsifiers on the basis of glycerol, polyglycerol, sorbitan and saccharose.

Since they are not poisonous and irritating and often well compatible with cosmetic and pharmaceutical components, the products prepared from polyalcohols and polyalcohol glycosides can be used, not only for technical and e.g. agricultural applications, but particularly for application in cosmetic and pharmaceutical products, e.g. as a surfactant, emulsifier, solubility promoting agent, dispersing agent, wetting agent, in washing agents (also for the washing of e.g. agricultural products), in cosmetic oil-in-water and water-in-oil creams, in shampoos, lotions, tooth paste, in medicinal ointments, vitamin oils, etc.

They are especially suitable for use in foodstuffs, e.g. to enable a good preparation, to facilitate this preparation and to improve the qualities of the products.

The emulsifiers can perform a great deal of functions, such as emulsifying and stabilising of emulsions, disperging, wetting, promoting the solubility, promoting the hydratation, controlling the forming of foam (introduction of air), complexing of starch and/or proteins, modifying of crystal and crystallisation, modifying the viscosity of the components, improving the consistency and/or texture of the products, anti-spattering agent, anti-oxidant.

Among other things they can be used: for the preparation of emulsified products, such as margarine, mayonnaise, salad dressing e.g. in order to increase the stability of the emulsions; for the preparation of various soft drinks, for the stabilisation of various emulsions of odorous and flavouring substances; for the preparation of bread, cake and confectionery, in which the workability of the dough is improved and a baked product with a better volume and an improved crumb structure and keeping qualities is obtained; as a lubricant for baking plates; in farinaceous foodstuffs, such as spaghetti, macaroni, vermicelli, in order to obtain the required boiling qualities; in "instant" products, such as cake mixes, dessert, pulverised coffee and tea, cocoa powder, milk- and egg-powder, dried soups; in confectionery, e.g. candy toffees and caramels, chewing gum; in chocolate to influence the viscosity and the crystallisation of the fatty phase; in ice creams, various desserts; in "toppings" (increase of volume, more tolerancy in the whipping period and superior stability of the product); in "coffee whiteners", milk products, confectioners' icing and -creams; in margarine and frying fat as an anti-spattering agent; for the preparation of edible coatings for the preservation of foodstuffs; for the preparation of peanut butter. Especially higher esterified reaction products of polyalcohols and/or polyalcoholglycosides and fatty acids from drying oils, can be suitable components for the preparation of resins for the paint industry.

EXAMPLE I 1,014 g Of a 70% sorbitol solution (3.9 mol) and 677 g palmitic acid (fatty acid compositions: 60% palmitic acid, 40% stearic acid; 2.5 mol) were introduced into a reactor and heated to 80°C. After the melting of the fatty acid the water was removed by distillation at reduced pressure, meanwhile the temperature was increased to 120°C. Thereupon, 143,5 g sodium soap (fatty acid composition: 50% palmitic acid, 50% stearic acid) was added and the temperature increased to 155°C.

The reaction was carried out for 8.5 hours under proper stirring at a reduced pressure of 40–120 mm Hg, a small quantity of an inert gas (nitrogen) being passed over the reaction liquid. After 6.5 hours the reaction mixture had become completely homogeneous; the acid value was then 11.8 (mg KOH per g). 1,470 g brown reaction product was obtained, the acid value was 3.0 and the saponification value 94.8. Only 4.1% of the polyalcohol used was converted into the anhydrocompounds sorbitan and isosorbide. The reaction product was purified, non-fatty-acid esterified sorbitol and soap were removed as follows.

500 g Reaction product was dissolved in an equal quantity of warm butanone and the soap was acidified with 20 g of 85% phosphoric acid. Thereupon, the non-esterified sorbitol, the sodium phosphate and the excess of phosphoric acid were eliminated by 2 extractions with 300 g water at a temperature of 70°C. It appeared that the extracted sorbitol could be recycled very well after decoloration by activated charcoal and desalting with ion exchange resins.

The greater part of the free fatty acid was eliminated by stirring the butanone phase for 30 minutes with a suspension of 11 g calcium hydroxide and filtration of the precipitated calcium soaps; the solution of sorbitol fatty acid ester in butanone was decolorised with 10 g activated charcoal.

Thereupon, the solvent was removed at a reduced pressure. 337 g cream to light brown coloured sorbitol palmitate was obtained having an acid value of 8.0 and a saponification value of 144.5; the purity of the ester was about 93%.

By means of a melting point microscope a melting range of 71°–74°C was measured.

It appeared that, with the purifying method used, there was no decomposition of the esters.

From a thin layer chromatographic analysis it appeared that the sorbitol palmitate consisted of:

55% mono-fatty acid esters,
33% di-fatty acid esters, and
12% esters with 3 or more fatty acid ester groups for each sorbitol group.

The reaction temperature was 145°C. The reaction proceeded well; in all examples homogeneous reaction products were obtained.

Further particulars concerning the reactions and the results are given in Table A.

Table A.

| Example | Mol ratio sorbitol: fatty acid to be esterified | Fatty acid soap prepared "in situ" from: (parts by weight per 100 parts by weight of sorbitol) | Reaction time (hour) | % of fatty acid esterified | % sorbitol converted into anhydro-compounds |
| --- | --- | --- | --- | --- | --- |
| III | 1.0 | 25.0 potassium carbonate | 14 | 95.7 | 4.8 |
| IV | 1.0 | 25.2; lithium hydroxide | 14 | 98.4 | 5.0 |
| V | 1.4 | 50.0; sodium formate | 11 | 97.0 | 5.8 |
| VI | 1.3 | 34.7; sodium propionate | 9 | 92.5 | 3.1 |

Remarks:
1. Ratio mono fatty acid esters: di-fatty acid esters: higher esters:
    Example III   = 47:36:17
    Example IV    = 43:38:19
2. In the examples V and VI about 15-20% of the added volatile organic acid is esterified with sorbitol.

EXAMPLE II

In this example the preparation in situ of a sodium soap is illustrated.

1,014 g Of a 70% sorbitol solution and 810 g palmitic acid were introduced into a reactor and heated to 80°C. After distilling the water 39.6 g of a 50 percent sodium hydroxide solution in water was added.

The esterification was effected in the manner as described in example I; no differences in the course of the reaction were noted. 1,479 g Product having an acid value of 2.9 and a saponification value of 95.0 was obtained; 3.9% of the quantity of sorbitol used was converted into anhydrocompounds.

500 g Product were partially purified; upon dissolving of the product in 300 g warm n-butanol and acidification of the soap with 23 g citric acid (0.7 mol per equivalent sodium), the non-esterified sorbitol was eliminated by 3 extractions with 250 g water at 70°-80°C. 357 g light brown colored product with an acid value of 30.7 and a saponification value of 159.1 was obtained; the free fatty acid percentage was 14.3 (a quantity equivalent to the NaOH and free fatty acid quantity in the reaction product).

EXAMPLES III–VI.

The preparation of sorbitol palmitate in the presence of lithium, sodium and potassium soaps prepared in situ with the use of a number of different alkali metal compounds is illustrated. The reactions were effected in the manner as described above. Lithium hydroxide and potassium carbonate were added to the mixture of anhydrous sorbitol and molten fatty acid. In the examples V and VI a mixture of a 70% sorbitol solution and the sodium salt of the volatile organic acid was made waterfree at a reduced pressure, after which the fatty acid was added.

Various qualities of sorbitol with different mannitol percentages (from < 1% by weight to about 8% by weight on the dry substance) were used; similar results were obtained; depending on the residual sugar content of the sorbitol differently coloured reaction products were formed. Also, anhydrous crystalline sorbitol (melting point 93°–95°C) could be successfully used as starting material.

EXAMPLES VII–XII

In these examples the influence of the reaction temperature and the soap contents are illustrated.

Equimolar quantities of sorbitol and palmitic acid were esterified as described above. In the experiments sodium soap (fatty acid composition: 50% stearic acid, 50% palmitic acid) is added, except in example X, where the soap was prepared in situ by adding anhydrous sodium carbonate. The reactions were effected at reduced pressure; it was noted (examples XI and XII) that similar results could be obtained by elimination of water by passing a relatively large quantity of inert gas (e.g. nitrogen) through the reaction liquid. If the reaction water was distilled at atmospheric pressure, a longer reaction time was required.

The reactions can yet be accelerated by eliminating the water in a more efficient way, e.g. in a thin film evaporator.

Particulars concerning the experiments and the results are given in Table B.

With highly different temperatures good products were obtained. The required reaction times were shorter when the temperatures and the soap percentages were higher.

From example VII it follows that the composition of the ester product is modified in favour of the mono-fatty acid ester component at a lower degree of esterification.

Table B.

| Example | parts by weight of fatty acid soap per 100 parts of sorbitol | reaction temperature (°C) | reaction time (hour) | % of fatty acid esterified | % sorbitol converted into anhydro-compounds |
| --- | --- | --- | --- | --- | --- |
| VII | 20 | 125 | 23 | 75.1 | 2.3 |

Table B.-continued

| Example | parts by weight of fatty acid soap per 100 parts of sorbitol | reaction temperature (°C) | reaction time (hour) | % of fatty acid esterified | % sorbitol converted into anhydro-compounds |
|---|---|---|---|---|---|
| VIII | 75 | 125 | 16 | 96.2 | 1.9 |
| IX | 20 | 145 | 14.5 | 97.2 | 4.6 |
| X | 50 | 145 | 8.5 | 97.5 | 3.5 |
| XI | 20 | 165 | 7.5 | 96.5 | 6.3 |
| XII | 50 | 180 | 2 | 96.8 | 7.1 |

Ratio mono-fatty acid esters: di-fatty acid esters: higher esters:
Example  VII:   50:35:15
         VIII:  45:36:19
         IX:    44:36:20
         X:     45:37:18

EXAMPLES XIII–XV

In the reaction of polyalcohol with fatty acid, besides mono-fatty acid esters, di-fatty acid esters and higher esters are also formed.

In these examples it is demonstrated that, in the present process, the quantity of mono-fatty acid ester in the product, sorbitol palmitate, can be highly varied by adjustment of the molecular ratio between polyalcohol and fatty acid, used in the reaction. The reactions were carried out at 155°C and a reduced pressure of 60–90 mm Hg in the presence of sodium palmitate prepared in situ by adding a 50% sodium hydroxide solution to the mixture of sorbitol and fatty acid after this mixture has been made waterfree (example II).

Further particulars concerning the reactions and the results are given in Table C.

In the experiments homogeneous products were obtained.

Table C.

| Example | mol ratio sorbitol: palmitic acid | parts by weight of fatty acid soap per 100 parts by weight of sorbitol | reaction time (hour) | % of fatty acid esterified | % of sorbitol converted into anhydro-compounds | composition of the fatty acid ester | | |
|---|---|---|---|---|---|---|---|---|
| | | | | | | mono- | di- | tri and higher |
| XIII | 0.2:1 | 50 | 18 | 86.0 | 18.1 | traces | 2 | 98 |
| XIV | 1.0:1 | 20 | 11 | 98.3 | 5.5 | 45 | 37 | 18 |
| XV | 3.0:1 | 15 | 8 | 97.3 | 3.9 | 67 | 26 | 7 |

Remark:
In example XIII a cream coloured ester was obtained after working up (purity about 91%; melting point 57–59°C.)
Similar highly esterified products could possibly serve also as a "low calorie" substitute for fats.

In the following comparative examples it is illustrated that the required products are not obtained if the reactions are carried out in a usual manner and not in the presence of the necessary quantity of fatty acid soap.

COMPARATIVE EXAMPLE a

1 Mol sorbitol and 1 mol palmitic acid were reacted for 30 hours at 145°C and a reduced pressure of about 80 mm Hg. The reaction mixture was well stirred. The reaction product consisted of 2 layers: a top layer containing the ester and free fatty acid, and a polyalcohol layer.

The acid value of the ester layer was 102, the saponification value 202; only 50% of the fatty acid was esterified. 18.3% of the sorbitol in the ester layer was converted into anhydrocompounds. The sorbitol palmitate contained about 15% di-fatty acid esters and 85% higher esterified components.

COMPARATIVE EXAMPLE b

1 Mol sorbitol and 1 mol palmitic acid were reacted for 34 hours at 155°C and a reduced pressure of 60–90 mm Hg, under good stirring.

0.9 g Anhydrous sodium carbonate (0.2% on the reaction mixture) was added as a catalyst. After 13 hours the acid value of the reaction product was still 85.0.

The final product was not homogeneous. An ester layer with an acid value of 17.4 and a saponification value of 168.5 was obtained; 33.4% of the sorbitol was converted into anhydrocompounds (31.1% into sorbitan and 2.3% into isosorbide).

The mono- and di-fatty acid ester percentage of the prepared ester was very low (13% and 18% respectively; 69% higher esters).

COMPARATIVE EXAMPLE c

1 Mol sorbitol and 1 mol palmitic acid were reacted for 5 hours at 145°C and a reduced pressure of 60 mm Hg; 0.9 g of p-toluene sulfonic acid was added as a catalyst. About 395 g of a homogeneous product was obtained. The acid value was 6.2 and the saponification value 143.1. Almost all the sorbitol was converted into anhydrocompounds (16.8% mono anhydrosorbitol, sorbitan and 78.9% di-anhydrosorbitol, isosorbide).

EXAMPLES XVI–XIX

The preparation of sorbitol esters of other fatty acids than palmitic acid is illustrated. Sorbitol esters are prepared from: Stearic acid (about 90% stearic acid), example XVI, technical oleic acid (a mixture of mainly unsaturated fatty acids with an oleic acid content of about 60%), example XVII, lauric acid (about 90% lauric acid), examples XVIII and XIX. The fatty acid soaps were prepared in situ by adding a 50 percent sodium hydroxide solution, except in example XVIII, where sodium palmitate was used.

The reaction temperature was 145°C in example XVI; in the examples XVII, XVIII and XIX this was 150°–155°C. The reaction products were partially purified in the manner as described in example II. In example XVI free fatty acids were removed by precipitation as calcium soaps; in the examples XVII and XIX the product could be deacidified by a (molecular) distillation (150°–180°C; very low pressure, about 0.1 mm Hg). Further particulars concerning the reactions and the results are given in Table D.

the starting materials was heated under nitrogen until the reaction components had molten and was then reacted at a reduced pressure of 80 mm Hg, under good stirring. Homogeneous products of a colour varying from almost white to light brown were obtained. The reaction products were purified in the manner as described in example I.

It appeared that the fatty acid soap could be well acidified with 3–5 parts by weight of lactic acid per 100 parts by weight of reaction product. In example XXIII poorly water-soluble crystals of non-esterified dulcitol, which formed in the first water extraction, are elimi- Table D.

| Example | mol ratio sorbitol:fatty acid | parts by weight of fatty acid soap per 100 parts by weight of sorbitol | Reaction time (hours) | % of the fatty acid soap esterified | % of the sorbitol converted into anhydro-compounds | composition of the fatty acid soap esters (in the purified products) | | |
|---|---|---|---|---|---|---|---|---|
| | | | | | | mono- | di- | tri- and higher |
| XVI | 1.0 | 20.2 | 15 | 96.2 | 5.5 | 40 | 37 | 23 |
| XVII | 1.6 | 20.6 | 9.5 | 98.0 | 4.7 | 46 | 39 | 15 |
| XVIII | 2.0 | 20.8 | 7.5 | 97.0 | 3.7 | 61 | 31 | 8 |
| XIX | 1.6 | 15.6 | 8.5 | 98.4 | 4.4 | 54 | 35 | 11 |

| Purified products: Example | Yield purification (% of the reaction product) | Acid value mg KOH/g | Purity (%) | Melting point (°C) |
|---|---|---|---|---|
| XVI sorbitol-stearate | 78.7 | 4.9 | 94.3 | 81 – 84 |
| XVII sorbitol-oleate | 61.4 | 6.4 | 95.5 | (very viscous liquid) |
| XIX sorbitol-laurate | 63.7 | 5.9 | 96.3 | 63 – 66 |

Remarks:
1. The reaction products in the examples XVI and XVII show a slight turbidity; with about 23–25 parts by weight of fatty acid soap homogeneous reaction products were obtained with a somewhat increased mono-fatty acid ester percentage.
2. After a 4 hours' reaction in example XIX the reaction mixture became homogeneous; the acid value was 30.

EXAMPLES XX–XXIII

Preparation of the palmitic acid esters of some other polyalcohols than sorbitol.

Erythritol, xylitol, mannitol and dulcitol were esterified with palmitic acid (equimolar quantities) in the presence of 20 parts by weight of sodium soap (fatty acid composition: 50% palmitic acid, 50% stearic acid) per 100 parts by weight of polyalcohol. The mixture of nated by filtration.

Further data concerning the reactions and the results are given in Table E.

Consequently, by means of the method according to the invention, esters could also be prepared from other polyalcohols than sorbitol with comparable results.

Table E.

| Example | Polyalcohol | Melting point (°C) | Reaction temperature (°C) | Reaction time (hour) | % fatty acid esterified | % polyalcohol converted into anhydrocompounds |
|---|---|---|---|---|---|---|
| XX | Erythritol | 120–122 | 150 | 11 | 99.4 | <2 |
| XXI | Xylitol | 92–93 | 152 | 10.5 | 98.3 | 3.2 |
| XXII | Mannitol | 165–166 | 160 | 8 | 98.4 | 6.2 |
| XXIII | Dulcitol | 188–191 | 175–185 | 3 | 98.2 | about 12 |

| Purified products: Example | Yield purification (%) | Acid value | Saponification value | Purity (%) | Melting point (°C) |
|---|---|---|---|---|---|
| XX erythritol palmitate | 83.3 | 2.2 | 170 | 95.4 | 63–66 |
| XXI xylitol palmitate | 83.2 | 5.1 | 159 | 94.2 | 65–67 |
| XXII mannitol palmitate | 78.6 | 5.9 | 154 | 93.9 | 91–93 |
| XXIII dulcitol palmitate | 75.8 | 5.9 | 160 | 94.3 | 66–69 |

Remark:
Ratio mono-fatty acid esters: di-fatty acid esters: higher esters in example XXII:
= 44:34:22 purified.

In the examples XXIV–XXVII the preparation of fatty acid esters of some polyalcohol glycosides, according to the invention are illustrated.

EXAMPLE XXIV

Maltitol palmitate

From a mixture of 459 g of a 75 percent maltitol solution (4-α D-glucopyranosyl D-sorbitol, prepared by catalytic hydrogenation of maltose) and 268 g of palmitic acid (fatty acid composition: 60% palmitic acid, 40% stearic acid) the water was eliminated at reduced pressure (temperature 80°–120°C). Thereupon, 76.7 g sodium palmitate was added. The reaction was carried out under good stirring at a temperature of 160°–165°C and a pressure lower than 100 mm Hg, whereas a small quantity of nitrogen was passed over the reaction liquid. After 8.5 hours a homogeneous, brown coloured reaction product was obtained (665 g). The acid value was 2.2, the saponification value 81.6; 97.3% of the fatty acid to be esterified had reacted. A thin layer chromatographic analysis showed that the maltitol palmitate was composed of:
- 39% mono-fatty acid esters,
- 46% di-fatty acid esters,
- 15% esters with 3 or more fatty acid ester groups for each maltitol group.

From gas chromatographic analyses of the maltitol after hydrolysis of the esters and preparation of the trimethylsilyl derivatives of the polyalcohol glycoside (gas chromatography column with a stationary phase of 3% OV-17 on chromosorb W-AW-DMCS) it appeared that this was hardly converted at all (at any rate for less than 5 to 10%) into anhydrocompounds etc.

The reaction product was purified; for that purpose 500 g were dissolved in 1,000 ml ethyl acetate at 70°C; after acidifying of the soap with 25 g of 85% phosphoric acid the non-esterified maltitol was extracted at 70°C with three times 200 ml water. After desalting by means of ion exchanging resins and decolorisation with active carbon, about 70–80 g maltitol was recovered from the combined water phases, which could be used again.

By cooling of the warm ethyl acetate solution to about 40°C a water phase separated, containing maltitol palmitate. After two more washings with 200 ml water at 35° to 40°C 143 g product A was obtained from the ethyl acetate phase after elimination of the solvent.

Upon extraction with two times 500 ml n-butanol, a decolorisation treatment and subsequent elimination of the solvent, 270 g of a light colored product B was obtained from the combined water layers.

The product A contained the greater part of the free fatty acid and mainly higher esterified maltitol palmitate. Analyses: acid value: 66.0;
- saponification value: 155;
- ratio mono-fatty acid: di-fatty acid: higher esters = 17:48:35.

The product B was composed of the purified maltitol palmitate. Analyses: acid value: 10.3;
- saponification value: 114;
- purity: 94,6%
- ratio mono-fatty acid: di-fatty acid: higher esters = 47:44:9;
- melting point: 73°–77°C.

EXAMPLE XXV 488 g Of a catalytically hydrogenated highmaltose syrup (containing about 10% hexitol; 55% maltitol; 15% hydrogenated maltotriose) with a dry substance content of 70.5% was evaporated at 50°–120°C and a pressure of 20 mm Hg. To the very viscous syrup was added 180 g palmitic acid and 69 g sodium palmitate.

The reaction was carried out at 165°C under nitrogen and at a reduced pressure with proper stirring.

After 10 hours 575 g brown coloured reaction product was obtained; the acid value was 4.5, the saponification value 66.6. About 15% of the hexitol was converted into anhydro-compounds. The fatty acid esters were composed of 13% sorbitol esters (4% mono-fatty acid esters, 7% di-fatty acid esters, 2% higher esters) and 87% sorbitol glucoside esters (mainly maltitol esters and a relatively small quantity of esters of the diglucoside malto triitol);
- 34% mono-fatty acid esters;
- 39% di-fatty acid esters;
- 14% higher esters.

EXAMPLE XXVI

Lactitol palmitate 485 g Of a 71% lactitol solution (4-β D-galactopyranosyl D-sorbitol prepared by catalytic hydrogenation of lactose) and 180 g palmitic acid were brought into a reactor and heated to 80°C. After the fatty acid had molten the water was removed by distillation under reduced pressure, while the temperature was increased to 120°C. Thereupon, 51.5 g sodium soap (fatty acid composition: 50% palmitic acid and 50% stearic acid) was added and the temperature was raised to 160°C.

The reaction was carried out for 9 hours under a good stirring at a reduced pressure of 20–80 mm Hg, a small quantity of nitrogen was passed over the reaction liquid. After 6.5 hours the reaction mixture became homogeneous; the acid value was 6.

560 g Brown colored reaction product with an acid value of 1.4 and a saponification value of 66.5 was obtained.

500 g Reaction product was purified in the manner as described in example I; however, as a solvent n-butanol was used. The temperature was 80°–90°C.

About 300 g purified product was obtained with an acid value of 9.6, a saponification value of 116.5 and a purity of about 91%; by means of a melting point microscope a melting range of 69°–72°C was measured.

The lactitol palmitate was composed of:
- 49% mono-fatty acid esters,
- 37% di-fatty acid esters,
- 14% higher esters.

EXAMPLE XXVII

From a mixture of 485 g 71% lactitol solution and 232 g lauric acid (purity about 90%) the water was removed. Thereupon, 12.2 g of a 50% sodium hydroxide solution was added. The reaction was carried out for 11 hours at 155°–160°C under nitrogen at a reduced pressure of about 80 mm Hg; the reaction mixture was well stirred.

560 g Of a homogeneous reaction product with an acid value of 3.6 and a saponification value of 97.9 was obtained.

500 g Reaction product was purified in the manner as described in example II. The major part of the free fatty acid could be removed by distillation at a reduced pressure (about 5 mm Hg; 160°–180°C; passage of steam). 340 g Purified lactitol laurate was obtained; the acid value was 8.7, the saponification value 143.4, the purity about 93% and the melting point 62°–65°C.

The lactitol laurate was composed of:
38% mono-fatty acid esters;
50% di-fatty acid esters;
12% higher esters.

EXAMPLE XXVIII

With the method according to the invention emulsifying agents can be prepared with HLB-values varying between wide limits. The rate of hydrophilly of non-ionic emulsifying agents can be compared by means of the hydrophilic-lipophilic balance (HLB) introduced by Griffin; the maximal HLB of a completely hydrophilic non-ionic emulsifying agent is 20. HLB values calculated according to the Griffin formula (J. Soc. Cosmetic Chemists 5, 249 (1954)):

$$H.L.B. = 20 \left(1 - \frac{\text{saponification value of the ester}}{\text{acid value of the fatty acid}}\right).$$

are given in Table F.

Table F.

| $C_nH_{n+2}(OH)_n$ | Tetritol n = 4 | Hexitol n = 6 | Hexitol glycoside (maltitol; lactitol) |
|---|---|---|---|
| monolaurate | 6.8 | 9.0 | 12.4 |
| trilaurate | 2.0 | 3.5 | 6.5 |
| monostearate | 5.4 | 7.3 | 10.7 |
| tristearate | 1.5 | 2.6 | 5.1 |

For, among other things, ionic emulsifying agents the HLB can be approximately calculated from the structure of the emulsifying agent, by totalizing the contributions of the various hydrophilic and lipophilic groups (J. T. Davies, Proc. 2nd Intern. Congr. Surface Activity 1, 426 (1957)):

HLB = 7 + Σ (hydrophilic group values) − Σ (lipophilic group values)

Some group values are:
- COONa group, group value: 19.1
- COOH group, group value: 2.1
- OH group, group value: 1.9
- Ester group, group value: 2.4
- $Ch_2$, $-CH_3$ group, group value: (−) 0.475

In this manner the influence of esterification of the polyalcohol esters with organic acids on the HLB of the emulsifying agent formed can be demonstrated. Esterification of 1 mol acid per mol polyol fatty acid ester increases the HLB value of emulsifying agent with a value:
- lactic acid: 1.4
- malic acid: 3.5
- tartaric acid: 5.4
- citric acid: 7.3

Neutralization of the free carboxylic groups of a di- or tricarboxylic acid esterified with polyalcohol fatty acid esters gives a clear change in the emulsifying behaviour.

In the following examples it is illustrated that by esterification of the polyalcohol fatty acid esters with e.g. food acids, products with modified properties can well be prepared and that in these reactions the number of anhydrocompounds of the polyalcohol remains small, so that a large part of the original polyalcohol hydroxylic groups remains available (with sorbitol esters an average of at least 5.5 non-etherified groups per molecule, to only about 3.6 groups with sorbitanesters).

It is known that by a similar modification many valuable products, which are used chiefly in the preparation of foodstuffs, are obtained from glycerol esters of fatty acids (so in using a trivalent alcohol)(e.g. aceto-glycerides, lactoglycerides, citric acid esters and (mono- and diacetyl) tartaric acid esters of mono- and diglycerides, stearylmono-glyceridylcitrate).

The preparations are illustrated with sorbitol palmitate as polyalcohol fatty acid ester.

EXAMPLES XXIX–XXXIII

Esters of sorbitol palmitate and lactic acid were prepared. 500 g Purified sorbitol palmitate, prepared according to example I, were reacted for 10 hours with a 90% solution of pharmaceutical grade lactic acid (72% directly titratable acid, 18% titratable after hydrolysis; degree of polymerisation 1.25) at a reduced pressure of 20–40 mm Hg, under nitrogen. In the examples XXX and XXXI 500 g partly purified sorbitol palmitate was used, prepared according to example II. In example XXXIII the cyclic dimer of L(+)-lactic acid, L-L-dilactide (melting point: 95°–96°C), was used; the reaction took place for 8 hours at atmospheric pressure, under nitrogen. Homogeneous reaction products were obtained; these were purified. Lactic acid and polylactic acid not esterified with sorbitol palmitate were eliminated from the product which was dissolved in 400 g butanone, by two extractions with 250 g water at a temperature of 70°C. After distilling the solvent, light colored products were obtained.

From thin layer chromatographic analyses of the products it appeared that new components with different retention times were formed, especially with the mono-fatty acid esters.

Further data concerning the reactions and the products are given in Table G.

In using a normal acid esterification catalyst, p-toluene sulfonic acid, good results were obtained (example XXXI); also suitable were, among other things: phosphoric acid and an ion exchange resin, e.g. Amberlyst 15: a macro-reticular sulfonic acid resin. Good results were also obtained in using non polymerised lactic acid (95% mono-lactic acid).

Volatile impurities can be eliminated from the products by means of a deodorising treatment (e.g. at 150°C and low pressure, about 1 hour's passage of steam).

TAble G.

| Example | Lactic acid 90% Solution (g) | Temperature (°C) | Weight (g) | % Sorbitol converted into anhydro-compounds | Purified product acid value | Purified product ester value | Purified product lactic acid contents (%) | Purified product melting point (°C) |
|---|---|---|---|---|---|---|---|---|
| XXIX | 240 | 100 | 575 | 7.5 | 15.6 | 215 | 16.4 | 52–54 |
| XXX | 240 | 120 | 610 | 11.0 | 36.6 | 241 | 23.5 | 46–47 |
| XXXI | 240 | 95 | 595 | 9.5 | 45.5 | 214 | 20.0 | 48–50 |
| XXXII | 80 | 110 | 538 | 6.9 | 13.0 | 177 | 8.9 | 58–61 |

Table G.-continued

| Example | Lactic acid 90% Solution (g) | Temperature (°C) | Weight (g) | % Sorbitol converted into an-hydro-compounds | Purified product acid value | ester value | lactic acid contents (%) | melting point (°C) |
|---|---|---|---|---|---|---|---|---|
| XXXIII | (148) | 110 | 580 | 14.1 | 15.2 | 218 | 17.5 | 52–55 |

Remarks:
1. Example XXXI: 0.5 g p-toluene sulfonic acid added as a catalyst.
2. Example XXXIII: 106 g dilactide used.

EXAMPLES XXXIV–XXXVI

Lactic acid esters of sorbitol palmitate were prepared by re-esterification of non-purified reaction product with esters of lactic acid and some volatile alcohols; during the reaction the low boiling alcohols were removed from the reaction mixture.

350 g Sorbitol palmitate (reaction product prepared according to example II) was treated during 6.5 hours at a temperature of 145°C with the respective lactic acid ester in a reactor equiped with a distillation fractionating column.

The pressure was regulated in such way that the lactic acid ester boiled under reflux and the volatile alcohol formed during the reaction distilled (from atmospheric pressure to 100 to 200 mm Hg). After the end of the reaction the remaining quantity of lactic acid ester was eliminated at a reduced pressure of a few mm Hg. In example XXXV a somewhat turbid reaction product was obtained, in example XXXVI a small underlayer consisting of sorbitol lactate could be separated. Before the removal of the remaining lactic acid esters all reaction mixtures were homogeneous. During the reactions the major part of the fatty acid soap was converted into sodium lactate and free fatty acid; a small quantity of ethyl esters of fatty acids and acyl lactates was formed. In the three examples an almost equal quantity of lactic acid was esterified with sorbitol palmitate and sorbitol; the reaction velocities were slightly different, after 3 hours 1.40 mol methanol was distilled, in example XXXIV,
1.20 mol ethanol in example XXXV,
1.05 mol butanol in example XXXVI.

A partly purified product was obtained by extracting the reaction products twice with 250 g water at a temperature of 90°–95°C; the major part of the sorbitol lactate and of the lactic acid not esterified with sorbitol palmitate was eliminated in this manner.

Further data concerning the reactions and the products obtained are given in Table H.

In some comparative examples another possible method is described for the preparation of mixed fatty acid and lactic acid esters of sorbitol, that is, the preparation of sorbitol lactate and esterification of the sorbitol lactate with palmitic acid.

COMPARATIVE EXAMPLE d 260 g Of a 70% sorbitol solution and 200 g of a 90% solution of pharmaceutical grade lactic acid were brought into a reactor. For 10 hours an esterification reaction was carried out at a temperature of 100°C and a reduced pressure of 20–30 mm Hg, under nitrogen.

325 g Reaction product with an acid value of 63.9 and a saponification value of 333.2 was obtained; 15.5% of the sorbitol was converted into anhydrocompounds.

268 g Palmitic acid and 1 g p-toluene sulfonic acid were added.

Heating took place for 9 hours under good stirring at a temperature of 95°–100°C and a reduced pressure of about 50 mm Hg. After 3 hours the reaction mixture became homogeneous; the acid value was 50.3; 97.4% of the sorbitol was converted into anhydrocompounds (73.1%) into sorbitan and 24.3% into isosorbide).

545 g reaction product with an acid value of 13.0 and a saponification value of 299 was obtained. The sorbitol was almost entirely converted into anhydrocompounds (68.8% into monoanhydrosorbitol, sorbitan and 29.4% into dianhydrosorbitol, isosorbide).

COMPARATIVE EXAMPLE e

Sorbitol lactate was prepared by means of a re-esterification reaction with ethyl lactate, in analogy with the method described in example XXXV.

182 g Crystalline sorbitol and 296 g ethyl lactate were reacted for 6.5 hours at 145°C; 40 g sodium lactate was added as a catalyst and as a miscibility promoting agent.

360 g Reaction product was obtained; the acid value was 7.1, the lactic acid contents 58% 14.7% of the sorbitol was converted into anhydrocompounds.

Table H.

| Example | lactic acid ester: weight (g) | weight of reaction product (g) | Purified product weight (g) | acid value | saponification value | % of the sorbitol converted into an-hydro-compounds |
|---|---|---|---|---|---|---|
| XXXIV | 240; methyl lactate | 466 | 335 | 16.0 | 232 | 9.6 |
| XXXV | 272; ethyl lactate | 465 | 341 | 14.3 | 235 | 9.3 |
| XXXVI | 336; butyl lactate | 462 | 332 | 8.1 | 224 | 10.4 |

Remarks:
1. Example XXXIV: bound lactic acid contents purified product: 17.1%
2. Example XXXV: bound lactic acid contents purified product: 17.7%.
   melting point purified product : 52–56°C.
   purity purified product : about 82%.
   (The product contained yet about 8% sorbitol lactate and 3% ethyl esters of fatty acids and fatty acid esters of lactic acid).

268 g Palmitic acid was added and for 16 hours an esterification reaction was carried out at a temperature at 145°C and a reduced pressure of about 80 mm Hg, under nitrogen. After 12 hours the mixture became homogeneous.

600 g Brown colored reaction product was obtained.
Analyses:
acid value: 17.1.
saponification value: 272.
% sorbitol converted into anhydrocompounds: 32.8.

In the esterification reaction with palmitic acid about 15–20 parts by weight of sodium fatty acid soap per 100 parts by weight of sorbitol were formed in situ.

In comparison with, among other things, example XXIX, XXXI and XXXV the use of the sorbitol fatty acid ester as starting material is clearly advantageous, to prevent as much as possible the formation of anhydrocompounds, of the polyalcohol.

EXAMPLE XXXVII

Esterification of sorbitol palmitate with acetic acid.

300 g Partly purified sorbitol palmitate (prepared according to example II) was reacted for 5 hours with 227 g acetic anhydride in the presence of 6 g sodium acetate at a temperature of 100°–105°C.

Thereupon, the formed acetic acid and the unreacted acetic anhydride were distilled at a reduced pressure and a temperature of 100°–125°C.

392 g Reaction product was obtaned, which was purified after solution in 500 ml butanone by two extractions with 300 ml water at 60°C.

An odorless solid product could be prepared by deodorizing for a few hours with steam at a temperature of 160°–180°C and a pressure of 5–10 mm Hg; in this treatment part of the non-esterified fatty acid was also eliminated.

350 g Purified light brown coloured acetic acid ester of sorbitol palmitate was obtaned.
Analyses:
acid value: 11.4
value: 410
hydroxyl value: 12
% of the sorbitol converted into anhydrocompounds: 12.5
melting point: 28°–30°C.

By modification of the number of fatty acid and acetyl groups, esters with highly varying melting points can be prepared.

EXAMPLES XXXVIII–XL.

Partly ionic emulsifying agents are prepared by esterification of a number of food acids, containing several carboxyl groups, with sorbitol palmitate.

300 g Purified sorbitol palmitate was esterified with 60 g malic acid (D-L, melting point 129°C), tartaric acid (L(+); melting point (170°C) or citric acid monohydrate.

The reactions took place at a reduced pressure of 20–30 mm Hg, under nitrogen; the reaction mixture was well stirred.

Homogeneous reaction products were obtained; in example XXXIX a small quantity of tartaric acid crystal was still present.

The reaction products obtained in examples XXXVIII and XXXIX were purified; the non-sorbitol palmitate-esterified acids were removed by means of one extraction with 300 g water and two extractions with 150 g water after dissolving the reaction product in 500 ml butanone at a temperature of 60°C. Thereupon, the solvent was distilled at a reduced pressure (temperature 100°C).

The products showing an acid reaction may be used as such; however, the non-sorbitol palmitate-esterified carboxylic groups can also be entirely or partially neutralized with suitable alkaline reacting substances to, e.g. the sodium, potassium and/or ammonium salts.

In example XXXVIII the sodium salt of the malic acid ester of sorbitol palmitate could be obtained by adding 8.6 g 50 percent sodium hydroxide solution to the solution of 100 g purified product in butanone and subsequently distilling the solvent. By this treatment the surface active properties of the product were clearly modified.

Further data concerning the reactions and the products are given in Table J.

Table J.

| Example | XXXVIII | XXXIX | XL |
|---|---|---|---|
| acid | malic acid (d-l) | tartaric acid | citric acid |
| reaction temperature $10^3$ (°C) | 110 | 110 | 105 |
| reaction time (hour) | 4 | 5 | 7 |
| Product |  |  |  |
| weight (g) | 338 | 334 | 346 |
| acid value | 60 | 45 | 86 |
| % sorbitol converted into anhydrocompounds | 17.4 | 22.1 | 14.2 |
| acid content (%) | 14.1 | 12.5 | 15.7 |
| number of acid groups esterified per molecule acid | 1.1 | 1.2 | 1.3 |
| melting point (°C) | 56–59 | 55–58 | 65–68 |

In the synthesis of the modified polyalcohol fatty acid esters, a polyalcohol fatty acid ester with few anhydrocompounds, i.e. with relatively many free hydroxyl groups, is more satisfactory as a starting material, as is evident when comparing, e.g. sorbitol palmitate with glycerol- and sorbitan esters of fatty acids; products with higher contents of watersoluble organic acid can be obtained, the reactions are more complete and fewer losses appear because homogeneous reaction mixtures are obtained more easily and less insoluble (polymeric) by-products are formed.

In a reaction of 100 parts by weight of mixtures containing monoglycerides (about 60% and 40% glycerol monopalmitate/ stearate, 1.0% free glycerol) with 20 parts by weight of citric acid monohydrate for 3–4 hours at 120°C. and a reduced pressure, insoluble gummy lower layers (about 1 and 6% respectively of the weight of the reaction product), consisting of polymeric glycerol-citric acid esters, separated, due to which products with a relatively low citric acid content were obtained.

In the reaction of sorbitol palmitate with citric acid a homogeneous reaction product was obtained even when the free sorbitol content was 3–5%.

Better results were also obtained in the preparation of tartaric acid esters and (partially) acetylated tartaric acid esters; good homogeneous products could be prepared in using tartaric acid with a relatively very low degree of acetylation.

COMPARATIVE EXAMPLE f 300 g Sorbitan monostearate (Span 60; a commerical product of Atlas Chemical Industries Inc., U.S.A.) was reacted with 60 g malic acid under circumstances similar to those given in example XXXVIII.

The reaction product was not homogeneous, 50 g of a lower layer separated. The ester layer was purified; the malic acid content of the purified products was 4.4%; only 21% of the malic acid used appeared to be converted into the malic acid ester of sorbitan monostearate.

The properties of polyalcohol fatty acid esters can also be modified by re-esterification with complete esters of di- and tri-carboxylic acids and volatile alcohols (e.g. tri-ethyl citrate), in which reaction the formed volatile alcohols are distilled from the reaction mixture; no free carboxylic groups containing mixed esters of the acids with e.g. sorbitol palmitate and ethanol are prepared.

A product with good emulsifying qualities is also obtained by esterification of the polyalcohol fatty acid ester with a partial ester of the acid containing more carboxylic groups and a (high boiling) alcohol, in which reaction the (fatty) alcohol is not eliminated from the reaction mixture.

EXAMPLE XLI 300 g Purified sorbitol palmitate was esterified with 250 g monostearyl citrate (saponification value 340; acid value 203) for 4 hours at a temperature of 110°C and a reduced pressure. 540 g reaction product was obtained; the acid value was 41; 12.7% of the sorbitol was converted into anhydrocompounds.

The product was a good emulsifying agent in shortenings e.g. for the preparation of cakes, in margarine and whip toppings, particularly in combination with other emulsifying agents (e.g. sorbitol lactopalmitate and glycerol lactopalmitate).

EXAMPLE XLII

An ester of acetylated tartaric acid and sorbitol palmitate was prepared.

While stirring, 100 g tartaric acid was added to 170 g acetic acid anhydride; nitrogen was passed over the reaction mixture. An exothermal reaction took place, the tartaric acid dissolved slowly and the temperature increased to 85°C; thereupon, the reaction mixture was heated to 120°C, at which temperature the acetic acid formed started boiling under reflux. After 30 minutes the reaction was terminated.

A solid, sticky product consisting of mono- and diacetyl tartaric acid (anhydride) can be obtained by distilling the formed acetic acid (120°–130°C, 20 mm Hg pressure) but the process can be executed more simply by using the liquid acetylation product directly for the esterification with sorbitol palmitate.

After adding 300 g molten purified sorbitol palmitate (mono-fatty acid ester content about 45%; acid value 7) the acetic acid was distilled in about 20 minutes at a temperature of 90°–$\phi$°C and a pressure of 10–20 mm Hg.

The reaction was then continued for 10 hours at 95°–100°C and a pressure of 20 mm Hg. The reaction mixture was homogeneous during the whole experiment. 432 g Product were obtained.

Analyses:
acid value: 90 (about 50% of the tartaric acid carboxylic groups were esterified) mol.acetic acid esterified per mol. tartaric acid: 1.65 % of the sorbitol converted into anhydrocompounds: 19.2 melting point: 47°–50°C.

The product was an excellent baking aid.

In the same manner and with practically similar results a (partial) ester of propionic acid and tartaric acid is also reacted with sorbitol palmitate (using 100 g tartaric acid and 217 g propionic acid anhydride; refluxing for 30 minutes at 140°–145°C).

We claim:
1. A process for the preparation of a carboxylic acid ester of a linear aliphatic polyalcohol or of a hydrophilic derivative of said polyalcohol, in which process the formation of polyalcohols containing anhydro-rings during the esterification reaction is minimized, said process comprising esterifying an aliphatic fatty acid having 10 to 22 carbon atoms with a polyalcohol or a glycoside of said polyalcohol in the presence of a fatty acid soap, in a quantity of about 10% to 80% based upon the polyalcohol, at a temperature between 100° and 190°C while sumultaneously eliminating water formed during the reaction said polyalcohol being a linear aliphatic polyalcohol of the formula $C_nH_{n+2}(OH)_n$ wherein $n$ is at least 4.

2. A process according to claim 1, wherein said polyalcohol is erythritol, arabitol, xylitol, sorbitol, mannitol or dulcitol.

3. A process according to claim 1, wherein mixtures of polyalcohols are used.

4. A process according to claim 1, wherein the glycosides contain glucose- or galactose units as the sugar component.

5. A process according to claim 4, wherein the glycosides are prepared by hydrogenation of reducing di- and oligosaccharides.

6. A process according to claim 1, wherein the glycosides consist essentially of hydrogenated maltose, hydrogenated lactose and hydrogenated technical maltose syrups.

7. A process according to claim 1, wherein mixtures of fatty acids are used.

8. A process according to claim 1, wherein the mol ratio of polyalcohol/ fatty acid is between 4:1 and 1:5.

9. A process according to claim 1 wherein the fatty acid soap is an alkali metal salt of the fatty acid or mixtures of fatty acids with 10–22 C-atoms.

10. A process according to claim 4, wherein the fatty acid soap is prepared in situ by adding alkali metal hydroxides, -bicarbonates, -carbonates or alkali metal salts of volatile organic acids to the reaction mixture.

11. A process according to claim 9 wherein the quantity of fatty acid soap is 10–80% by weight of the quantity of polyalcohol or polyalcohol glycoside.

12. A process according to claim 1 wherein the polyalcohol or polyalcohol glycoside fatty acid ester is reacted with a watersoluble organic acid with 2–6 carbon atoms or with anhydrides or esters thereof.

13. A process according to claim 12, wherein the organic acid with 2–6 carbon atoms, is acetic acid, propionic acid, lactic acid, glycolic acid, succinic acid, fumaric acid, maleic acid, malic acid, tartaric acid or citric acid.

14. A process according to claim 12, wherein organic acids with 2–6 carbon atoms are used, of which one to three carboxylic acid groups is esterified.

15. A process according to claim 12, wherein, in using acids containing more carboxylic groups, the carboxylic groups which have not reacted with polyalcohol fatty acid ester are entirely or partially neutralized.

16. A process according to claim 12 wherein the water soluble organic acids are hydroxy acids or anhydrides thereof, of which at least one or two hydroxy groups is esterified with one member selected from the group consisting of acetic acid and propionic acid.

17. A process as claimed in claim 1 comprising reesterifying the thusly obtained esters.

18. Esters of fatty acids having 10 22 carbon atoms and polyalcoholglycosides selected from the group consisting of: hydrogenated maltose, hydrogenated lactose and hydrogenated technical maltose syrups.

* * * * *

UNITED STATES PATENT AND TRADEMARK OFFICE
CERTIFICATE OF CORRECTION

PATENT NO. : 3,951,945
DATED : April 20, 1976
INVENTOR(S) : HEESEN ET AL

It is certified that error appears in the above-identified patent and that said Letters Patent are hereby corrected as shown below:

Between lines 8 and 9, insert the following:

Claims priority, application Netherlands, May 15, 1973, 73.06759

Signed and Sealed this

Eighteenth Day of October 1977

[SEAL]

Attest:

RUTH C. MASON
Attesting Officer

LUTRELLE F. PARKER
Acting Commissioner of Patents and Trademarks